(12) United States Patent
Lynn

(10) Patent No.: US 7,087,123 B2
(45) Date of Patent: Aug. 8, 2006

(54) CLEANING AND SANITIZING SYSTEM

(75) Inventor: Daniel W. Lynn, Bainbridge Island, WA (US)

(73) Assignee: Ozone International LLC, Bainbridge Island, WA (US)

(*) Notice: Subject to any disclaimer, the term of this patent is extended or adjusted under 35 U.S.C. 154(b) by 0 days.

(21) Appl. No.: 11/226,991

(22) Filed: Sep. 15, 2005

(65) Prior Publication Data

US 2006/0005861 A1    Jan. 12, 2006

Related U.S. Application Data

(62) Division of application No. 10/755,527, filed on Jan. 9, 2004.

(51) Int. Cl.
*B08B 7/04* (2006.01)
(52) U.S. Cl. .............................. 134/37; 134/31; 134/32; 134/42
(58) Field of Classification Search .................. 134/31, 134/32, 34, 37, 42; 422/26, 27, 28
See application file for complete search history.

(56) References Cited

U.S. PATENT DOCUMENTS

| 3,612,094 A | 10/1971 | Hare |
| 5,503,594 A | 4/1996 | Karubian et al. |
| 6,455,017 B1 | 9/2002 | Kasting, Jr. et al. |

*Primary Examiner*—M. Kornakov
(74) *Attorney, Agent, or Firm*—Black Lowe & Graham, PLLC

(57) ABSTRACT

A high pressure water stream (14) is discharged onto a surface to be cleaned. An ozone/water stream (16) is discharged on the same surface for sanitizing the surface. The high pressure water and ozone/water streams (14, 16) are discharged simultaneously along closely adjacent paths that are either parallel (FIG. 3) or concentric (FIG. 2). The water pressure is at least about 100 p.s.i. and is preferably between 100 p.s.i. and 1000 p.s.i. The nozzles that discharge the streams (14, 16) may be movable relative to the object(s) that receives the high pressure water and ozone/water (FIG. 1) Or, they may be fixed and the object may be movable relative to them (FIG. 4)

3 Claims, 5 Drawing Sheets

CLEANING AND SANITIZING SYSTEM

PRIORITY CLAIM

This application is a divisional of U.S. patent application Ser. No. 10/755,527 filed Jan. 9, 2004, the contents of which are hereby incorporated by reference.

FIELD OF THE INVENTION

This invention relates generally to cleaning by use of a high pressure water stream and sanitizing by use of an ozone/water stream and, more specifically, to a cleaning and sanitizing method and apparatus in which the high pressure water stream and the ozone/water stream are discharged together, closely adjacent each other but without mixing.

BACKGROUND OF THE INVENTION

The following United States Patents disclose apparatus and methods of using ozone together with a cleaning fluid: U.S. Pat. No. 5,236,512 granted Aug. 17, 1993, to Ernest E. Rogers, Blaine A. Frandsen and Lamont Hislop; U.S. Pat. No. 5,493,754, granted Feb. 27, 1996 to Russell Gurstein and Edgar York; U.S. Pat. No. 5,815,869, granted Oct. 6, 1998 to John M. Hopkins; U.S. Pat. No. 5,839,155, granted Nov. 24, 1998 to Edward D. Berglund, Sung K. Cho and Lowell H. Schiebe; U.S. Pat. No. 6,115,862 granted Sep. 12, 2000 to Theodore R. Cooper, Allyson T. Toney and John B. McParlane; U.S. Pat. No. 6,348,227, granted Feb. 19, 2002, to Luis D. Caracciolo; U.S. Pat. No. 6,455,017, granted Sep. 24, 2002, to John R. Kasting, Dwayne H. Joines and John D. Winings; U.S. Pat. No. 6,458,398, granted Oct. 1, 2002 to Durand M. Smith, Dale S. Winger and Joshuan Brown, and U.S. Pat. No. 6,638,364, granted Oct. 28, 2003 to Gene Harkins and John M. Hopkins.

U.S. Pat. No. 6,455,017 discloses various uses of ozone as a sterilant. In this patent, it is stated that ozone cannot be combined with detergent or other cleaning agents since these are vulnerable to ozone attack. It is also stated that the ozone will destroy both its own effectiveness and that of the cleaning agent rather than attacking pathogens. U.S. Pat. No. 6,455,017 discloses directing a detergent cleaning solution, preferably under pressure, onto a surface to be cleaned. Then following the removal of the soils by the detergent an aqueous ozone rinse is applied to the surface. It is stated that the ozone rinse functions to sanitize the object being cleaned and remove residual detergent. The method of U.S. Pat. No. 6,455,017 involves first directing the cleaning solution onto the surface under pressure, and then rinsing the surface by directing a flow of the ozonated water onto the surface.

U.S. Pat. No. 5,865,995, granted Feb. 2, 1999 to William R. Nelson, and U.S. Pat. No. 6,361,688, granted Mar. 26, 2002, also to William R. Nelson, disclose systems for producing "ozonated water", also termed "ozone/water". As well be described, the selected one of the systems is combined in a novel way in the system of the present invention.

An object of the present invention is to deliver a high pressure cleaning water stream and an ozone/water stream substantially simultaneously to a surface to be cleaned and sanitized. The invention is basically characterized by delivering the high pressure water stream and the ozone/water stream closely adjacent to each other but without mixing. The high pressure water stream removes particles from the surface and the ozone/water stream sanitizes the surface almost simultaneously.

SUMMARY OF THE INVENTION

The cleaning and sanitizing system of the present invention is basically characterized by a first discharge nozzle from which a stream of high pressure water is discharged and a second discharge nozzle from which a stream of ozone/water is discharged. The first and second nozzles are positioned adjacent to each other so that the water and ozone/water streams are contiguous but the ozone/water is not delivered in the high pressure water stream. The high pressure water stream is discharged at a pressure high enough that it will exert a cleaning force on a surface to be cleaned and would convert the ozone into oxygen if the ozone/water stream were to be delivered into the high pressure water stream. In preferred form, the pressure of the high water pressure stream is at least about 100 p.s.i. More preferably, the pressure of the high pressure water stream is between 100 p.s.i. and about 2000 p.s.i. The pressure of the ozone/water stream is smaller than the pressure of the high pressure water stream and is sufficiently small that the ozone is not converted into oxygen.

According to one aspect of the invention, the ozone/water stream concentrically surrounds the high pressure water stream.

According to another aspect of the invention, the high pressure water and the ozone/water are discharged as closely spaced substantially parallel stream.

The nozzles for discharging the high pressure water and the ozone/water can be movable to the object that is to be cleaned. Or, the discharge nozzles can be fixed and the article to be cleaned can be moved relative to the nozzles.

In an embodiment of the cleaning and sanitizing system of the present invention, a circulating flow path of ozone/water is provided. Along this path, one or more high pressure water discharge nozzles are provided. An ozone/water nozzle is associated with each high pressure water nozzle. The high pressure water stream may be used to "pump" or "aspirate" ozone/water from the circulating system. As ozone/water is removed from the system, new water is delivered to the ozone/water generator and additional ozone is added to the water in the generator.

Other objects, advantages, and features of the invention will become apparent. From the description of the best mode set forth below, from the drawings, from the claims and from the principles that are embodied in the specific structure that are illustrated and described.

BRIEF DESCRIPTION OF THE DRAWINGS

Preferred and alternative embodiments of the present invention are described in detail below with reference to the following drawings.

DETAILED DESCRIPTION OF THE INVENTION

Figure 1:
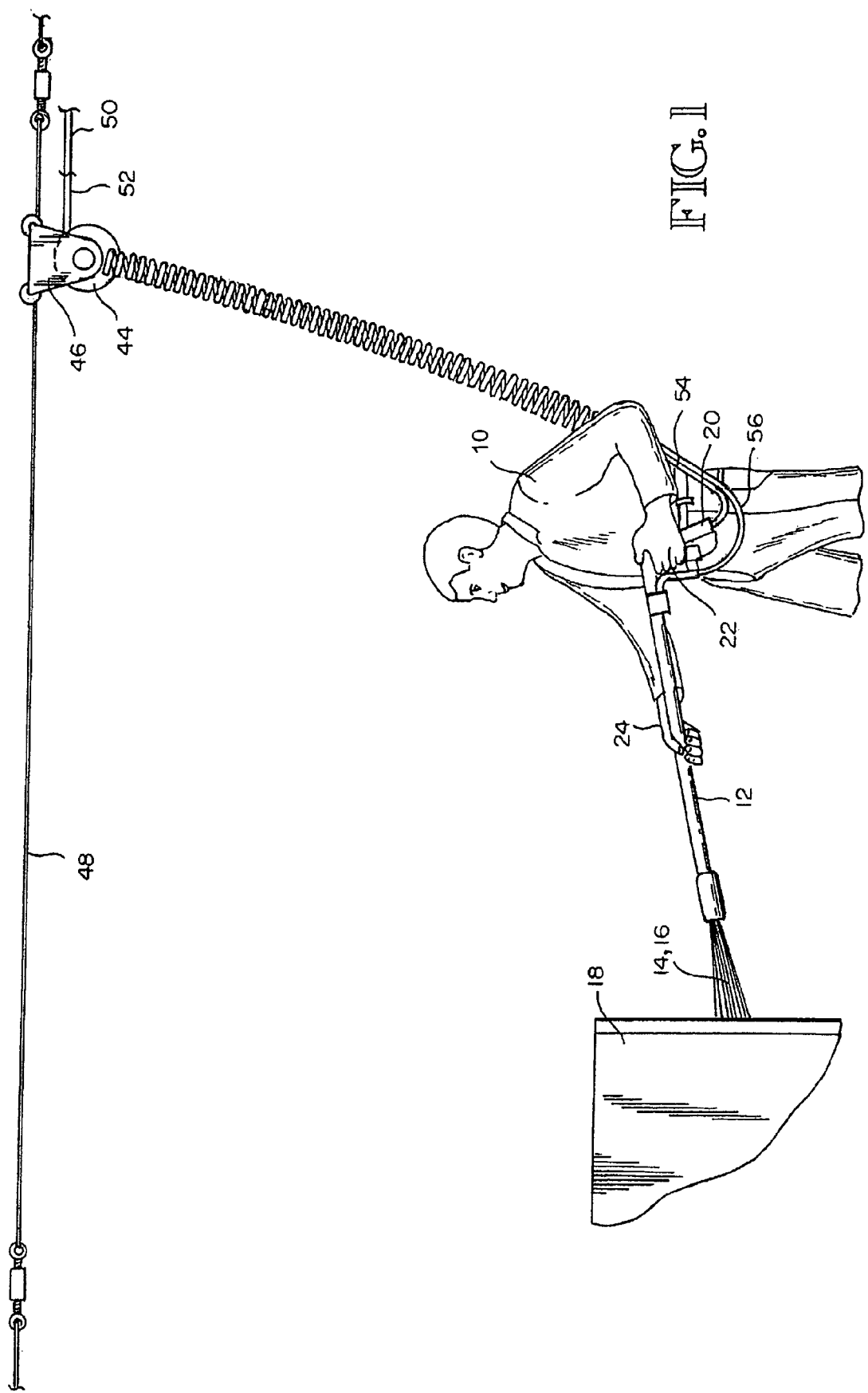
FIG. 1 is a fragmentary side elevational view showing a workman in the process of cleaning and sanitizing an object, by use of a high pressure water stream and an ozone/water stream.
Figure 2:
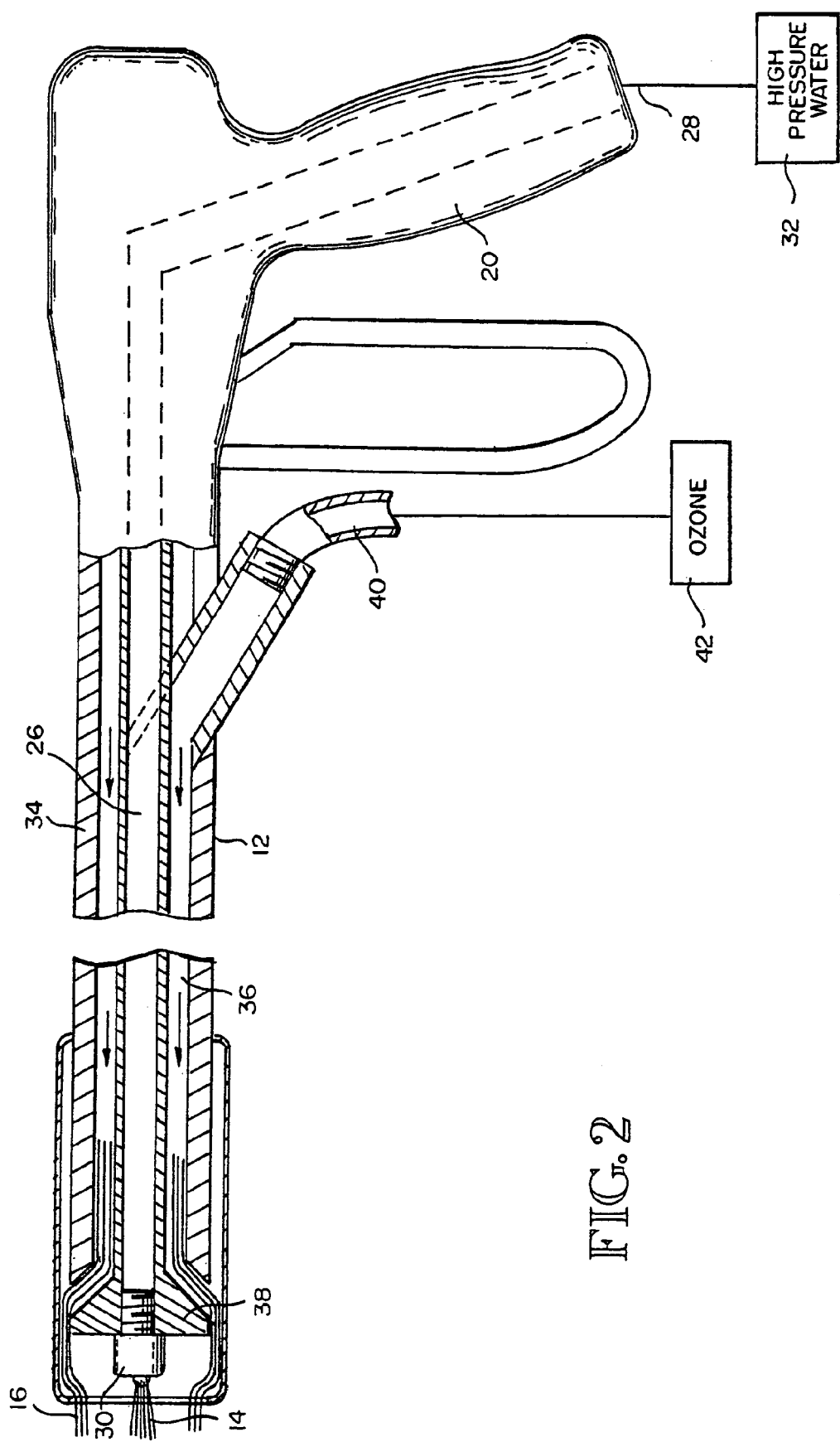
FIG. 2 is a side elevational view of the wand shown in FIG. 1, showing a portion of the wand in longitudinal section, such view showing a first nozzle discharging high pressure water stream surrounded by a second nozzle discharging an ozone/water stream.
Figure 3:
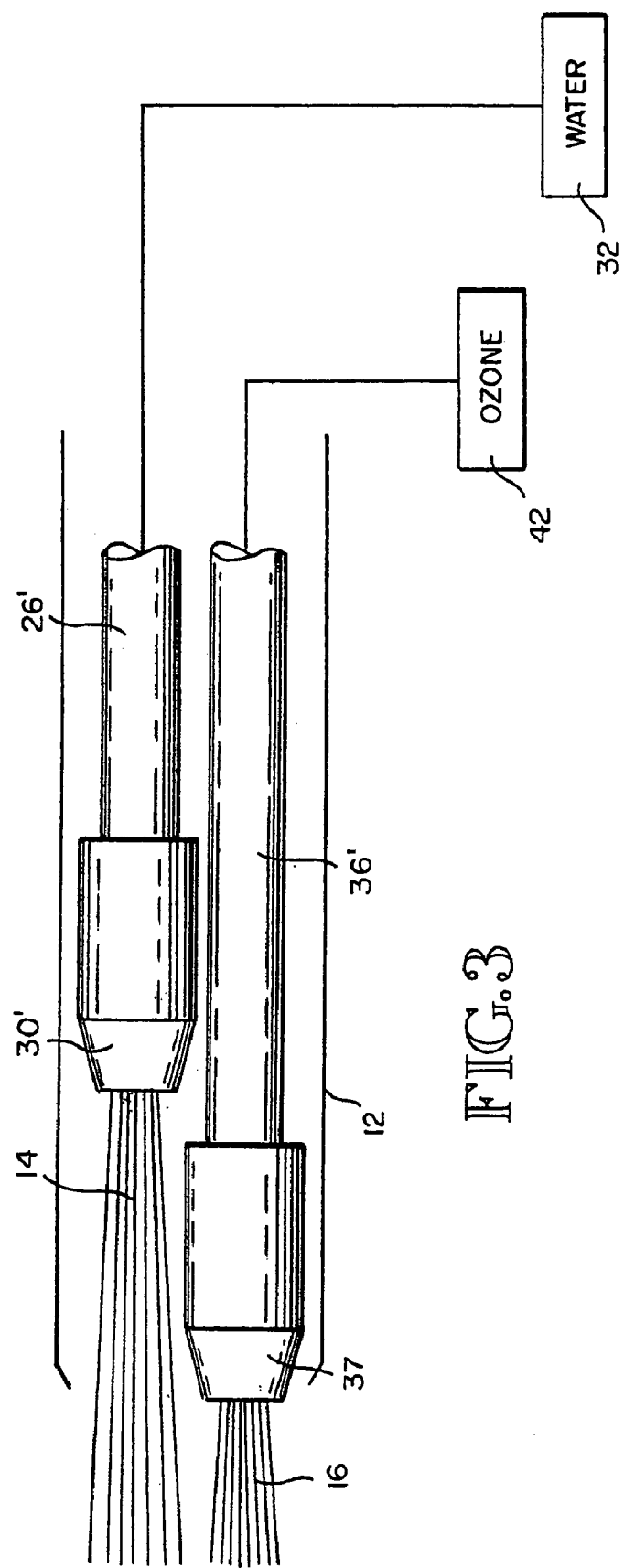
FIG. 3 is a somewhat schematic view of a second embodiment of the wand, showing the high pressure water nozzle and stream and the ozone/water nozzle and stream in a side-by-side relationship.

FIG. 1 shows a workman 10 holding a wand 12 that is adapted to discharge a high pressure water stream, for cleaning, and an ozone/water stream for sanitizing. The two streams 14, 16 are being discharge against an object 18 that needs to be cleaned and sanitized. FIG. 2 shows the high pressure water stream 14 surrounded by the ozone/water stream 16. FIG. 3 shows the high pressure water stream 14 and the ozone/water stream 16 being discharged in a side by side relationship.

Referring to FIG. 2, the wand 12 has a grip portion 20 that the workman 10 grips with one hand 22. The workman's other hand 24 grips an elongated central portion of the wand 12. In this embodiment, the wand 12 includes a conduit 26 that extends through the wand 12 from an inlet 28 to an outlet 30. The inlet 28 is connected to a source of high pressure water 32. The outlet 30 is in the form of a discharge nozzle that discharges a stream of the high pressure water 14. Wand 12 includes a tubular outer wall 34 that surround the high pressure water conduit 26. An annular passageway 35 is defined by and radially between the two tubular walls 26, 34. A cone 38 is provided at the outlet of the annular passageway 36. A conduit 40 delivers ozone from a source 42 into the passageway 36. The ozone/water flows through passageway 36, and through diagonal ports in cone 38 and discharges as an annular stream 16 surrounding stream 14, Streams 16, 14 do not directly impinge. They extend substantially parallel to each other along a relative small diameter combined stream path.

The conduits 28, 40 includes suitable on-off valves that are not shown. This is because they are not a part of the present invention but can be like the many valves that are available for controlling fluids that flow through conduits.

FIG. 3 shows a wand 12 that includes a high pressure water conduit 26' positioned closely adjacent an ozone/water conduit 36'. As previously described, the high pressure water stream 14 and the ozone/water stream 16 are discharged in close proximity to each other but neither infringes directly on the other. The ozonated water is sprayed through an opening 37. There is no attempt to mix the ozone/water stream 16 with the high pressure water stream 14. As is well known by a person of ordinary skill in the art, the high pressure water conduit 26' will include an off/on valve and the ozone/water stream 36' will also include an off/on valve. The valves may also control the pressure and discharge flow rate of the two streams 14, 16, in a known matter.

FIG. 1 shows an overhead hose reel 44 on a pulley 46. Pulley 46 is adapted to travel along a rod or a line 48. The reel 44 is preferably a dual reel. It supports a high pressure water hose 50 and an ozone/water hose 52. As the worker 10 walks forwardly from the position shown in FIG. 1, the pulley 46 will move forwardly on the rod or line 48. In a manner that is known to those skilled in the art, a first coiled hose 54 and a second coil hose 56 extend downwardly from the reel 44. The coils 54, 56 are in the nature of coil springs. They will extend when the operator 10 and the wand 12 move forwardly. They will retract when the operator 10 and the wand 14 move rearwardly.

Figure 4:
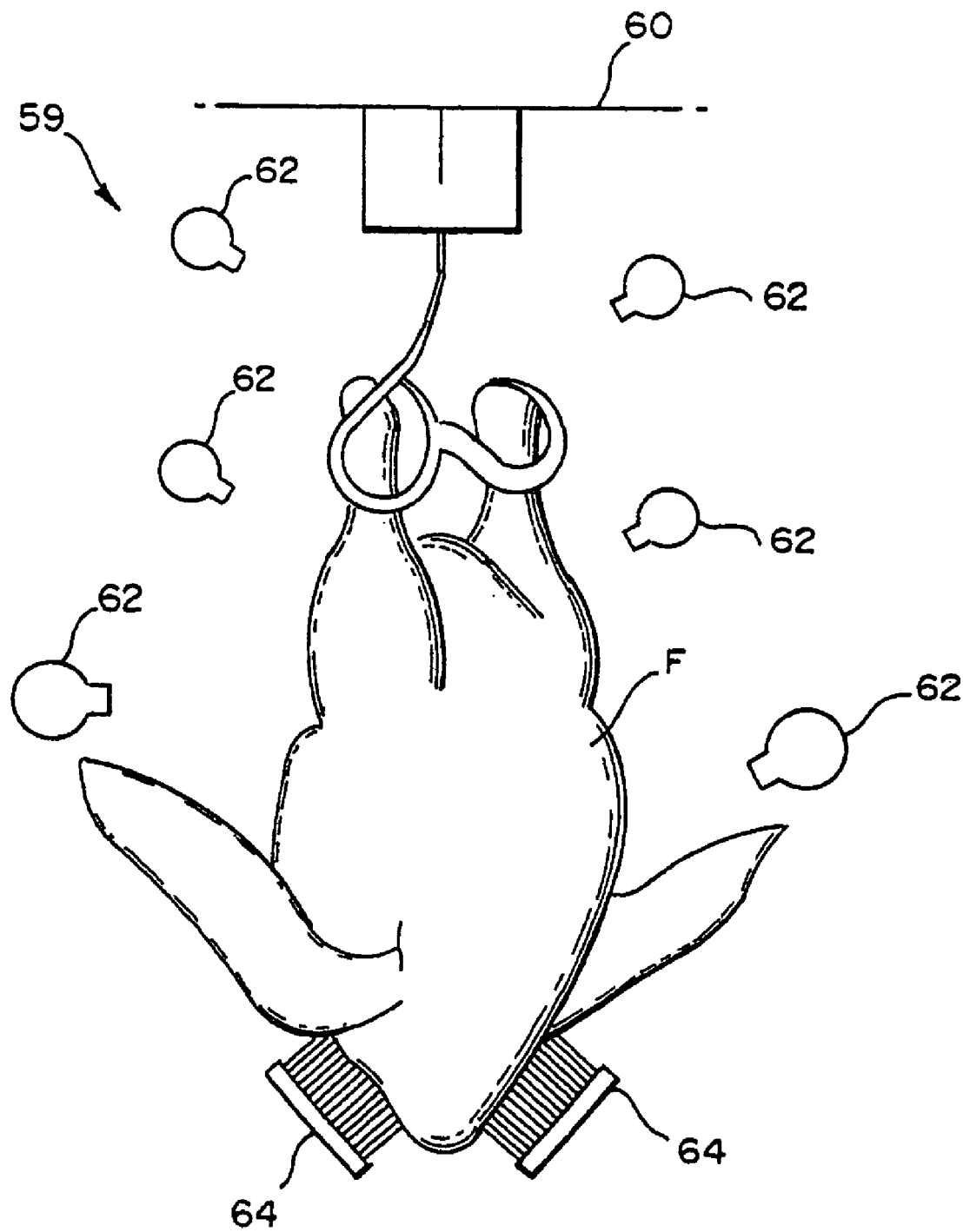
FIG. 4 is a view of an apparatus for conveying chickens or other fowl along a path that is between stationary nozzles for delivering a high pressure water stream, for cleaning the fowl, and an ozone/water stream, for sanitizing the fowl.

FIG. 4 is substantially like FIG. 6 in the aforementioned U.S. Pat. No. 6,348,227 B1. A conveyor 60 is shown conveying a fowl F. (e.g. a chicken or a turkey) or some other animal or object along a path, through a processing area between high pressure water and ozone/water streams discharging from nozzles 62. In addition to the nozzles 62, the system 59 may include brushes 64 as described in U.S. Pat. No. 6,348,227 B1. The nozzles 62 are constructed to discharge a stream of high pressure wash water 14 closely adjacent a stream of ozone/water, but without direct mixing of the two streams.

As has been described, the high pressure water stream 14 and the ozone/water stream 16 may be brought to the object or article to be cleaned and sanitized. Or, the high pressure water stream 14 and the ozone/water stream 16 may be discharged from stationary nozzles (e.g. nozzles 62) towards a moving object or objects (e.g. fowl that are moved relative to the stationary nozzles 62).

Figure 5:
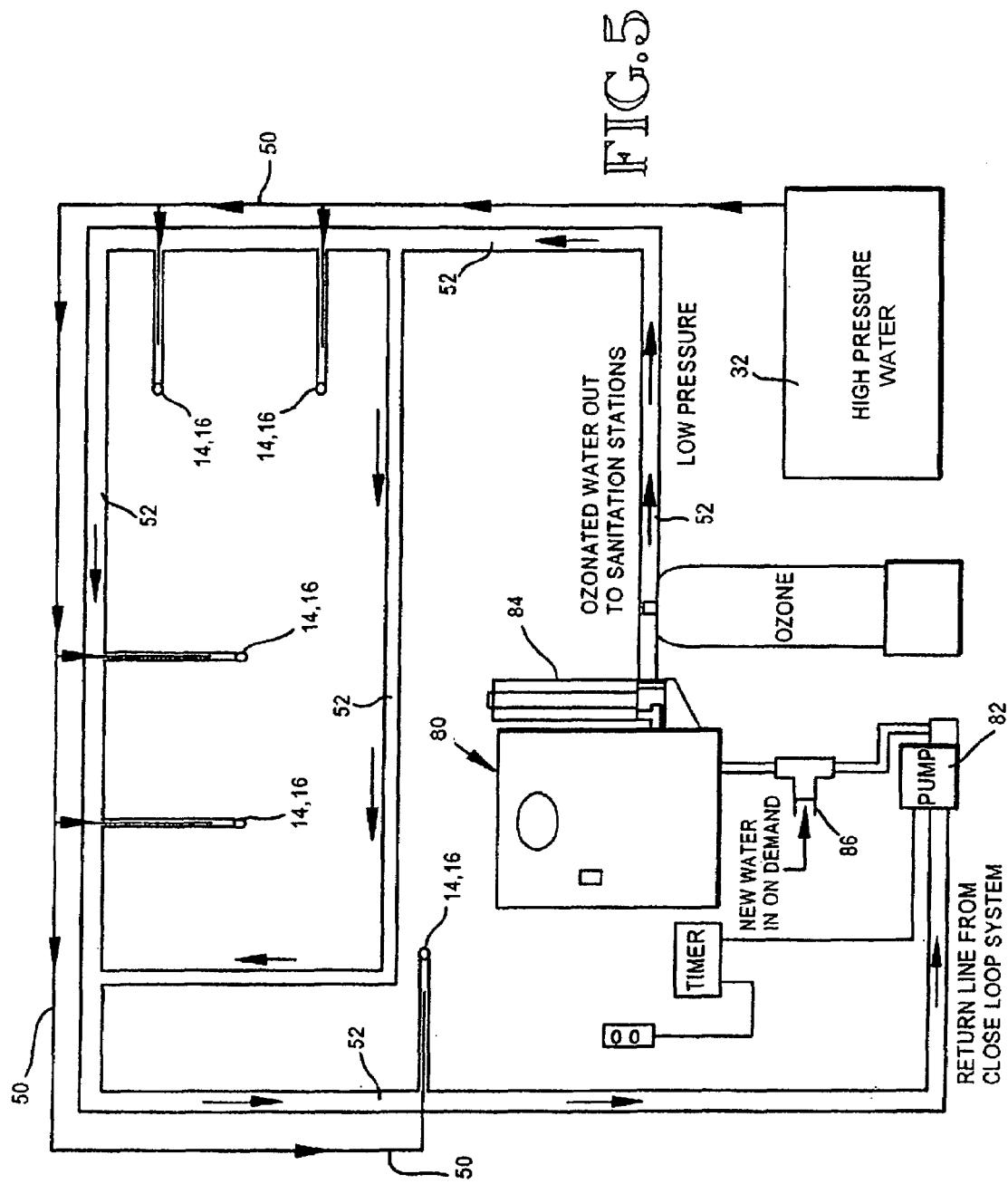
FIG. 5 is a flow diagram of a system embodying the present invention.

FIG. 5 shows a cleaning and sanitizing system that utilizes the present invention. High pressure water is pumped from source 32 into conduit 50 and from conduit 50 to the nozzle 30 (shown in FIG. 2), 30' (shown in FIG. 3) that forms the high pressure water stream 14. Ozonated water (ozone/water) is delivered from apparatus 80 into conduit 52 which leads to nozzles from the ozone streams 16. The apparatus 80 for admixing ozone to water may be one of the apparatuses disclosed in the aforementioned U.S. Pat. Nos. 5,865, 995 and 6,361,688. The contents of these patents are hereby incorporated herein by this specific reference.

The ozonated water conduit 52 forms a closed loop with the apparatus 80. A pump 82 pumps the ozone/water in conduit 52 to the recirculated liquid inlet of a contact tank 84. See inlet 112 in U.S. Pat. No. 6,361,688 leading into contact tank 36 disclosed in that patent. The high pressure water stream 14 will pump or aspirate the ozone/water and remove it from the closed loop conduit 52. Because some of the ozonated water is discharged from the water nozzles 30, 30', new water is added at 86 into admixture with the recirculated ozone/water that is moved by pump 82 into the inlet of the contact chamber 84.

Preferably, the cleaning water that is discharged from the nozzles 30, 30' is water only. That is, it does not include a detergent or some other chemical. The surface to be cleaned is cleaned by the force of the high pressure water stream rather than by a detergent or other additive to the water stream. The ozone/water stream is delivered directly on the surface that is being cleaned by the water stream and there is no chemical present with which the ozone may react.

The illustrated embodiments are only examples of the present invention, and therefore, are non-limitive. It is to be understood that many changes in the particular structure, materials, and features of the invention may be made without departing from the spirit and scope of the invention. Therefore, it is my intention that my patent rights not be limited by the particular embodiments that are illustrated and described herein, but rather are to be determined by the following claims, interpreted according to accepted doctrine of claim interpretation, including the use of the doctrine of equivalence.

The invention claimed is:

1. A method of cleaning an object, comprising providing a hand-held spraying device:

directing a first stream of high pressure water from the hand-held spraying device toward the object; and directing a second stream of ozone/water from the hand-held spraying device toward the object; wherein the steps of directing the first stream of high pressure water and directing the second stream of ozone/water are accomplished simultaneously.

2. The method of claim 1, wherein the first stream of high pressure water and the second stream of ozone/water are substantially parallel to one another.

3. The method of claim 1, wherein the first stream of high pressure water is adjacent to the second stream of ozone/water without admixing the ozone to the stream of high pressure water for a substantial distance.

* * * * *